(12) United States Patent
Jia

(10) Patent No.: US 11,084,013 B1
(45) Date of Patent: Aug. 10, 2021

(54) METAL-FREE CATALYTIC OXIDATION SYSTEM, AN OXYGENATION METHOD AND A METHOD FOR PRODUCING BENZOIC ACID DERIVATIVES

(71) Applicant: Zhejiang University of Technology, Zhejiang (CN)

(72) Inventor: Jianhong Jia, Zhejiang (CN)

(73) Assignee: Zhejiang University of Technology, Hangzhou (CN)

( * ) Notice: Subject to any disclaimer, the term of this patent is extended or adjusted under 35 U.S.C. 154(b) by 0 days.

(21) Appl. No.: 17/120,503

(22) Filed: Dec. 14, 2020

(30) Foreign Application Priority Data

Sep. 23, 2020  (CN) .......................... 202011011487.5

(51) Int. Cl.
| | | |
|---|---|---|
| *B01J 8/00* | (2006.01) | |
| *B01J 8/02* | (2006.01) | |
| *B01J 8/06* | (2006.01) | |
| *B01J 19/00* | (2006.01) | |
| *B01J 19/24* | (2006.01) | |
| *C07C 51/27* | (2006.01) | |
| *C07C 62/06* | (2006.01) | |
| *C07C 63/06* | (2006.01) | |

(52) U.S. Cl.
CPC .............. *B01J 8/065* (2013.01); *C07C 51/27* (2013.01); *B01J 2208/0053* (2013.01); *B01J 2208/00309* (2013.01); *C07C 63/06* (2013.01)

(58) Field of Classification Search
CPC ......... B01J 8/00; B01J 8/02; B01J 8/06; B01J 8/065; B01J 19/00; B01J 19/24; B01J 19/2425; B01J 19/2435; B01J 2208/00; B01J 2208/00008; B01J 2208/00017; B01J 2208/00106; B01J 2208/00309; B01J 2208/0053; B01J 2219/00; B01J 2219/24; C07C 51/00; C07C 51/16; C07C 51/27; C07C 63/00; C07C 63/04; C07C 63/06
See application file for complete search history.

(56) References Cited

U.S. PATENT DOCUMENTS 4,428,923 A * 1/1984 Kunkel ................ B01J 19/2435
                                                       423/588

* cited by examiner

*Primary Examiner* — Natasha E Young

(57) ABSTRACT

A metal-free catalytic oxidation system, an oxygenation method and a method for producing benzoic acid derivatives. The system includes a feed device; a tubular reactor; a plurality of venturi nozzles mounted on the tubular reactor at intervals; a tubular filter; a discharge device for a solid phase product; and an intermediate tank for reaction mixture. A low-pressure zone is formed at an output end of each of the plurality of venturi nozzles, and an oxygen inlet corresponds to the low-pressure zone; the tubular filter comprises an inner tube and an outer tube connected to each other, where the inner tube is provided with small holes for solid-liquid separation; the discharge device for the solid phase product is located at an end of the inner tube; and the intermediate tank for reaction mixture is connected to the outer tube of the tubular filter through a pipeline.

10 Claims, 1 Drawing Sheet

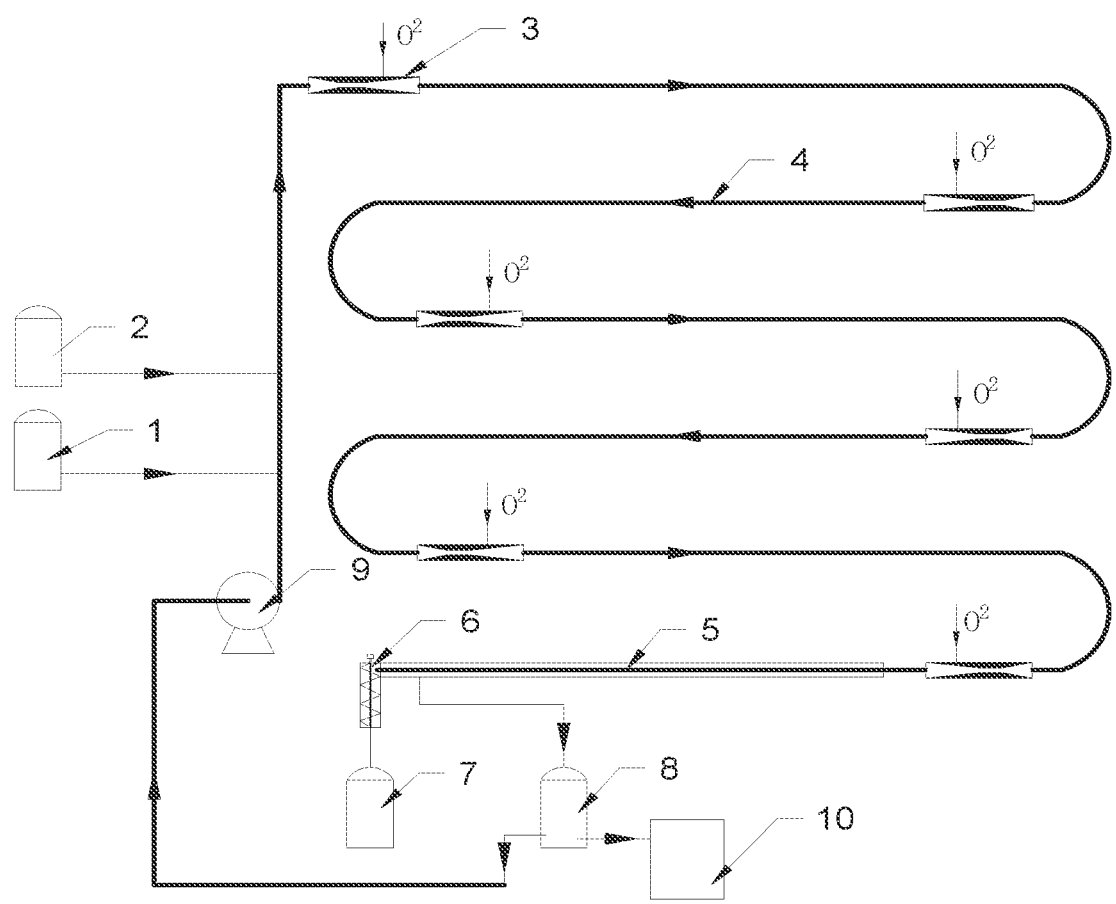

METAL-FREE CATALYTIC OXIDATION SYSTEM, AN OXYGENATION METHOD AND A METHOD FOR PRODUCING BENZOIC ACID DERIVATIVES

CROSS-REFERENCE TO RELATED APPLICATIONS

This application claims the benefit of priority from Chinese Patent Application No. 202011011487.5, filed on Sep. 23, 2020. The content of the aforementioned application, including any intervening amendments thereto, is incorporated herein by reference in its entirety.

TECHNICAL FIELD

The present application relates to metal-free catalytic oxidation systems, and more particularly to a metal-free catalytic oxidation system, an oxygenation method and a method for producing benzoic acid derivatives.

BACKGROUND

Oxidation reaction is a very important type of chemical reaction in the chemical industry that involves many chemical products, such as organic aldehydes, organic acids, etc. These compounds play a very important role in pharmaceuticals, dyes, pesticides and common chemicals. However, most oxidation reactions in the chemical industry occur in the presence of transition metals as catalysts, for example, toxic heavy metals such as chromium and vanadium, and noble metals such as chromium, vanadium, ruthenium, iridium, platinum, silver and gold. Loss of heavy metals can always be found when the metal catalysts participate in the reaction either in a liquid form (for homogeneous catalysis) or a solid form (for heterogeneous catalysis). This increases the production cost and causes serious heavy metal pollution to surrounding environments. The increase of the awareness of environmental protection brings an urgent demand for chemists to research and develop a green chemical process with the characteristics of atomic economy and sustainable development, so as to reduce toxic substances and waste gases produced during the chemical reaction and reduce energy consumption.

Oxygenation technology instead of traditional oxidation technology has become a major trend. Molecular oxygen is the cheapest and cleanest oxidant, and its oxidation byproduct is mainly water, so the oxygenation technology is an ideal oxidation method. But the molecular oxygen cannot directly oxidize the substrate under normal circumstances, it needs to be activated with the help of a suitable catalyst before it participate in the oxidation reaction. Therefore, the development of oxidation reaction has a trend towards the design and synthesis of green oxygenation technology to effectively and selectively synthesize various chemicals in the oxygenation process.

The oxidation reaction is strongly exothermic that is one of 18 dangerous systems. Most of the oxidation reactions in the industrial production have the characteristics of more instant heat release, unknown mechanism and fast reaction speed. Therefore, it is accompanied by disadvantages such as uncontrollability, more by-products and high risks. However, there are still many oxidation reaction systems that use intermittent production in the industrial production.

For a continuous production, various reaction materials are continuously added to a reactor in a certain ratio and at a constant speed, and the products are continuously discharged out of the reactor at a constant speed. The composition of the reactant, temperature and pressure at a particular part of the reactor are always constant. A tubular reactor is a kind of continuous operation reactor with a tubular shape and a large aspect ratio. Because the molecules of the reactant stay in the tubular reactor for the same time, the concentration of the reactant and the chemical reaction speed at any point of the tubular reactor do not change with time, only with the length of the tube of the tubular reactor. Specifically, the unit reactor volume of the tubular reactor has a larger heat exchange area, which is especially suitable for a reaction with larger thermal effect. And the reactant has a fast reaction speed and a fast flow rate in the tubular reactor, thereby obtaining a high productivity. It is concluded that the tubular reactor is suitable for a large-scale and continuous chemical production. Compared with a tank reactor, the tubular reactor has a reduced backmixing, and especially the flow pattern of fluid in the tube is close to the ideal subcritical flow under a lower flow rate. Therefore, the continuous tubular reaction has a simple and compact structure, high strength and safety, excellent corrosion resistance and impact resistance, long service life and easy maintenance.

Benzoic acid derivatives are an extremely important class of fine chemical products, which are widely applied in various fields such as pharmaceuticals, pesticides, dyes, food additives, plasticizers, feed additives, coatings, flavors and fragrances. However, the products are basically produced by oxidation of substituted toluene derivatives, which have a limited production, with an annual output ranging from tens of tons to thousands of tons, so there is basically a kettle-type batch production industrialization in industrial production.

SUMMARY

1. Technical Problems to be Solved

A first object of the present invention is to provide a metal-free catalytic oxidation system to overcome the defects in the prior art. It requires no metal catalyst to participate in the reaction, thereby reducing the cost and avoiding heavy metal pollution to the environment.

Based on the first object of the present invention, a second object of the present invention is to provide an oxygenation method using said metal-free catalytic oxidation system.

Based on the above two objects of the present invention, a third object of the present invention is to provide a method for producing benzoic acid derivatives by oxygenation using said metal-free catalytic oxidation system. This method will reduce the reaction risks, improve automatic levels, reduce labor intensity and human costs, improve and stabilize product quality, reduce pollutant emissions, and reduce energy consumption for unit of production.

2. Technical Solutions

Technical solutions of this application are specifically described as follows to achieve the above three objects associated with each other.

The present invention provides a metal-free catalytic oxidation system, comprising:
  a feed device;
  a tubular reactor;
  a plurality of venturi nozzles mounted on the tubular reactor at intervals;
  a tubular filter;
  a discharge device for a solid phase product connected to a solid phase output end of the tubular filter; and an intermediate tank for reaction mixture connected to a liquid phase output end of the tubular filter;

wherein a low-pressure zone is formed at an output end of each of the plurality of venturi nozzles, and an oxygen inlet corresponds to the low-pressure zone; the tubular filter comprises an inner tube and an outer tube connected to each other, wherein the inner tube is provided with small holes for solid-liquid separation; the discharge device for the solid phase product is located at an end of the inner tube; and the intermediate tank for reaction mixture is connected to the outer tube of the tubular filter through a pipeline.

In an embodiment, the feed device comprises a basic material feed device and a nitric acid feed device.

In an embodiment, a heat exchange system in the form of a sleeve is provided outside the tubular reactor, and a heat exchange medium flows in a gap between the heat exchange system and the tubular reactor.

In an embodiment, the plurality of venturi nozzles are spaced apart on the tubular reactor.

In an embodiment, the discharge device for the solid phase product is a screw conveyor.

In an embodiment, the intermediate tank for reaction mixture is provided with two bleeder tubes, where one is connected to an effluent treatment system, and the other is connected to the tubular reactor.

In an embodiment, the tubular reactor is provided with a circulating feed pump.

The present invention also provides an oxygenation method using the metal-free catalytic oxidation system.

The present invention further provides a method for producing benzoic acid derivatives by oxygenation using the metal-free catalytic oxidation system, comprising.

1) opening a nitric acid storage tank to add a certain amount of a nitric acid and then closing the nitric acid storage tank; and turning on the circulating feed pump to start circulation of materials in the system;

2) turning on a heat exchange system of the tubular reactor to heat the tubular reactor;

3) opening a raw material storage tank to introduce a raw material into the tubular reactor;

4) opening the nitric acid storage tank again to introduce the nitric acid into the tubular reactor;

5) opening the plurality of venturi nozzles to feed oxygen, the raw material and the nitric acid into the tubular reactor for reaction;

6) opening the intermediate tank for the reaction mixture to discharge excess effluent in the tubular reactor; and 7) turning on the screw conveyor to transport finished product in the tubular filter into a product storage tank.

In an embodiment, the raw material is any one of tert-butyltoluene, nitrotoluene, p-chlorotoluene,

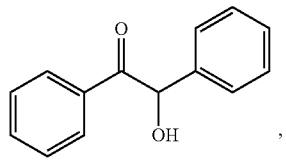 [SMILES: O=C(c1ccccc1)C(O)c1ccccc1]

2,4-dimethyl nitrobenzene,

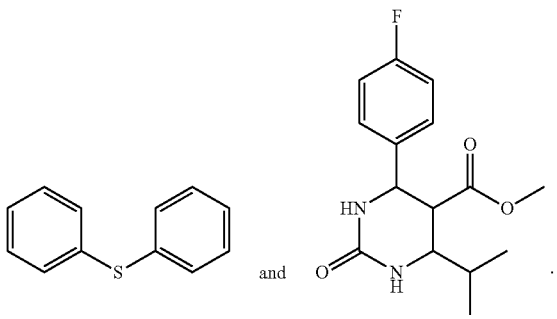 [SMILES: c1ccc(Sc2ccccc2)cc1 ; "and" ; COC(=O)C1C(c2ccc(F)cc2)NC(=O)NC1C(C)C ; "."]

The present invention has the following beneficial effects compared to the prior art.

3. Beneficial Effects

1) The present invention provides a metal-free catalytic oxidation system, an oxygenation method and a method for producing benzoic acid derivatives, which solves the problems of heavy metal pollution, difficulty in catalyst separation, and loss of catalysts caused by addition of metal catalysts in many oxidation reactions.

2) The present invention provides the metal-free catalytic oxidation system, the oxygenation method and the method for producing benzoic acid derivatives, in which the tubular reactor with the plurality of venturi nozzles and the tubular filter with automatic discharge, thereby solving the problems of difficult operation control, low production efficiency, poor safety, and unstable product quality caused by the intermittent tank reaction used in the current industrial production.

3) The plurality of venturi nozzles used herein are mounted in the tubular reactor, which solves the problem of insufficient gas-liquid mixing in a general tubular reactor. A sudden increase of a flow velocity at outlets of the venturi nozzles causes a pressure drop, which in turn leads to a rapid cavitation of liquid into small droplets that can quickly mix with incoming oxygen. At the same time, the increase of the flow velocity at the nozzles promotes the forward movement of solid oxides generated in a reaction mixture with the liquid with no blockage. Finally, the tubular reactor is provided with the venturi nozzles, which can not only supply oxygen in time required for the reaction, but also continuously promote the production of the solid oxides, thereby ensuring a high efficiency and stable production.

BRIEF DESCRIPTION OF THE DRAWINGS

The FIGURE is a schematic diagram of a metal-free catalytic oxidation system according to the present disclosure.

In the drawings: 1 raw material storage tank, 2 nitric acid storage tank, 3 venturi nozzle, 4 tubular reactor, 5 tubular filter, 6 screw conveyor, 7 product storage tank, 8 intermediate tank for reaction mixture, 9 circulating feed pump, 10 effluent treatment system.

DETAILED DESCRIPTION OF EMBODIMENTS

The technical solutions in the embodiments of the present disclosure will be clearly and completely described below with reference to the drawings. It is apparent that the embodiments disclosed below are only some embodiments of the present disclosure, not all of the embodiments. Any other embodiments can be made by those of ordinary skill in

Embodiment 1

1) Open the nitric acid storage tank, and close it after adding 100 kg of a 25% nitric acid solution to the system, and then open the circulating feed pump 9 to start the circulation of materials in the system.

2) Open the tubular reactor 4 and heat the tubular reactor 4 to raise the temperature of the system to 90° C.

3) Open the raw material storage tank 1 to introduce the p-tert-butyltoluene into the tubular reactor 4 at a feed rate of 100 kg/h.

4) Open the nitric acid solution storage tank again to continue to introduce the nitric acid solution into the tubular reactor 4 at a feed rate of 33 kg/h.

5) Open all venturi nozzles 3 to feed oxygen into the tubular reactor 4 at a total feed rate of 18.1 $m^3$/h.

6) Open the intermediate tank 8 for the reaction mixture to discharge the excess effluent in the tubular reactor 4 at a discharge rate of 30 kg/h.

7) Open the screw conveyor 6 to transport the synthesized p-tert-butylbenzoic acid in the tubular filter 5 into the product storage tank 7; wash the product in the storage tank with water and dry it; and finally analyze it by a high performance liquid chromatography. A purity of the p-tert-butylbenzoic acid is 99.5%; a production rate is 119.3 kg/h; and a molar yield is 99.2%.

8) Check and keep the concentration of nitric acid in the reaction mixture in the intermediate tank 8 every hour at no less than 24.5%. When the concentration of nitric acid is lower than 24.5%, the feed rate of nitric acid solution needs to be increased appropriately.

Embodiment 2

1) Open the nitric acid storage tank, and close it after adding 100 kg of a 30% nitric acid solution to the system, and then open the circulating feed pump 9 to start the circulation of materials in the system.

2) Open the tubular reactor 4 and heat the tubular reactor 4 to raise the temperature of the system to 90° C.

3) Open the raw material storage tank 1 to introduce the p-nitrotoluene into the tubular reactor 4 at a feed rate of 100 kg/h.

4) Open the nitric acid solution storage tank again to continue to introduce the nitric acid solution into the tubular reactor 4 at a feed rate of 33 kg/h.

5) Open all venturi nozzles 3 to feed oxygen into the tubular reactor 4 at a total feed rate of 19.4 $m^3$/h.

6) Open the intermediate tank 8 for the reaction mixture to discharge the excess effluent in the tubular reactor 4 at a discharge rate of 30 kg/h.

7) Open the screw conveyor 6 to transport the synthesized p-nitrobenzoic acid in the tubular filter 5 into the product storage tank 7; wash the product in the storage tank with water and dry it; and finally analyze it by a high performance liquid chromatography. A purity of the p-nitrobenzoic acid is 99.8%; a production rate is 120.4 kg/h; and a molar yield is 99.6%.

8) Check and keep the concentration of nitric acid in the reaction mixture in the intermediate tank 8 every hour at no less than 29.4%. When the concentration of nitric acid is lower than 29.4%, the feed rate of nitric acid solution needs to be increased appropriately.

Embodiment 3

1) Open the nitric acid storage tank, and close it after adding 100 kg of a 28% nitric acid solution to the system, and then open the circulating feed pump 9 to start the circulation of materials in the system.

2) Open the tubular reactor 4 and heat the tubular reactor 4 to raise the temperature of the system to 90° C.

3) Open the raw material storage tank 1 to introduce the p-chlorotoluene into the tubular reactor 4 at a feed rate of 100 kg/h.

4) Open the nitric acid solution storage tank again to continue to introduce the nitric acid solution into the tubular reactor 4 at a feed rate of 33 kg/h. 5) Open all venturi nozzles 3 to feed oxygen into the tubular reactor 4 at a total feed rate of 21 $m^3$/h.

6) Open the intermediate tank 8 for the reaction mixture to discharge the excess effluent in the tubular reactor 4 at a discharge rate of 30 kg/h.

7) Open the screw conveyor 6 to transport the synthesized parachlorobenzoic-acid in the tubular filter 5 into the product storage tank 7; wash the product in the storage tank with water and dry it; and finally analyze it by a high performance liquid chromatography. A purity of the parachlorobenzoic-acid is 98.5%; a production rate is 124 kg/h; and a molar yield is 99.7%.

8) Check and keep the concentration of nitric acid in the reaction mixture in the intermediate tank 8 every hour at no less than 27.4%. When the concentration of nitric acid is lower than 27.4%, the feed rate of nitric acid solution needs to be increased appropriately.

Embodiment 4

1) Open the nitric acid storage tank, and close it after adding 100 kg of a 25% nitric acid solution to the system, and then open the circulating feed pump 9 to start the circulation of materials in the system.

2) Open the tubular reactor 4 and heat the tubular reactor 4 to raise the temperature of the system to 90° C.

3) Open the raw material storage tank 1 to introduce

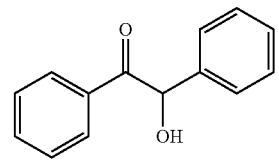 [SMILES: O=C(c1ccccc1)C(O)c1ccccc1]

into the tubular reactor 4 at a feed rate of 100 kg/h.

4) Open the nitric acid solution storage tank again to continue to introduce the nitric acid solution into the tubular reactor 4 at a feed rate of 33 kg/h.

5) Open all venturi nozzles 3 to feed oxygen into the tubular reactor 4 at a total feed rate of 12.6 $m^3$/h.

6) Open the intermediate tank 8 for the reaction mixture to discharge the excess effluent in the tubular reactor 4 at a discharge rate of 30 kg/h.

7) Open the screw conveyor 6 to transport the synthesized

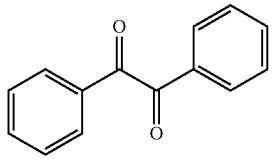 [SMILES: O=C(C(=O)c1ccccc1)c1ccccc1]

in the tubular filter 5 into the product storage tank 7; wash the product in the storage tank with water and dry it; and finally analyze it by a high performance liquid chromatography. A purity of

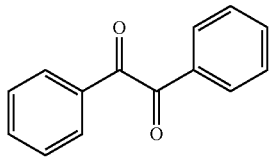 [SMILES: O=C(C(=O)c1ccccc1)c1ccccc1]

is 99.2%; a production rate is 98.2 kg/h; and a molar yield is 98.8%.

8) Check and keep the concentration of nitric acid in the reaction mixture in the intermediate tank 8 every hour at no less than 24.5%. When the concentration of nitric acid is lower than 24.5%, the feed rate of nitric acid solution needs to be increased appropriately.

Embodiment 5

1) Open the nitric acid storage tank, and close it after adding 100 kg of a 30% nitric acid solution to the system, and then open the circulating feed pump 9 to start the circulation of materials in the system.

2) Open the tubular reactor 4 and heat the tubular reactor 4 to raise the temperature of the system to 90° C.

3) Open the raw material storage tank 1 to introduce the 2,4-dimethyl nitrobenzene into the tubular reactor 4 at a feed rate of 100 kg/h.

4) Open the nitric acid solution storage tank again to continue to introduce the nitric acid solution into the tubular reactor 4 at a feed rate of 33 kg/h.

5) Open all venturi nozzles 3 to feed oxygen into the tubular reactor 4 at a total feed rate of 17.5 m³/h.

6) Open the intermediate tank 8 for the reaction mixture to discharge the excess effluent in the tubular reactor 4 at a discharge rate of 30 kg/h.

7) Open the screw conveyor 6 to transport the synthesized 3-methyl-4-nitrobenzoic acid in the tubular filter 5 into the product storage tank 7; wash the product in the storage tank with water and dry it; and finally analyze it by a high performance liquid chromatography. A purity of the 3-methyl-4-nitrobenzoic acid is 99.5%; a production rate is 118.1 kg/h; and a molar yield is 99.5%.

8) Check and keep the concentration of nitric acid in the reaction mixture in the intermediate tank 8 every hour at no less than 29.4%. When the concentration of nitric acid is lower than 29.4%, the feed rate of nitric acid solution needs to be increased appropriately.

Embodiment 6

1) Open the nitric acid storage tank, and close it after adding 100 kg of a 35% nitric acid solution to the system, and then open the circulating feed pump 9 to start the circulation of materials in the system.

2) Open the tubular reactor 4 and heat the tubular reactor 4 to raise the temperature of the system to 90° C.

3) Open the raw material storage tank 1 to introduce

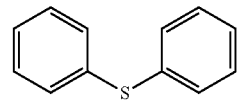 [SMILES: c1ccc(Sc2ccccc2)cc1]

into the tubular reactor 4 at a feed rate of 100 kg/h.

4) Open the nitric acid solution storage tank again to continue to introduce the nitric acid solution into the tubular reactor 4 at a feed rate of 33 kg/h.

5) Open all venturi nozzles 3 to feed oxygen into the tubular reactor 4 at a total feed rate of 14.4 m³/h.

6) Open the intermediate tank 8 for the reaction mixture to discharge the excess effluent in the tubular reactor 4 at a discharge rate of 30 kg/h.

7) Open the screw conveyor 6 to transport the synthesized

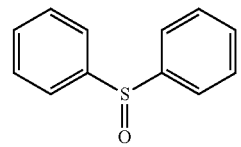 [SMILES: O=S(c1ccccc1)c1ccccc1]

in the tubular filter 5 into the product storage tank 7; wash the product in the storage tank with water and dry it; and finally analyze it by a high performance liquid chromatography. A purity of

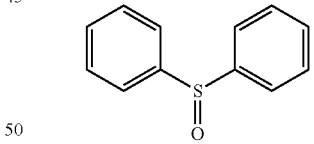

is 99.6%; a production rate is 107.5 kg/h; and a molar yield is 99.1%.

8) Check and keep the concentration of nitric acid in the reaction mixture in the intermediate tank 8 every hour at no less than 34.3%. When the concentration of nitric acid is lower than 34.3%, the feed rate of nitric acid solution needs to be increased appropriately.

Embodiment 7

1) Open the nitric acid storage tank, and close it after adding 100 kg of a 65% nitric acid solution to the system, and then open the circulating feed pump 9 to start the circulation of materials in the system.

2) Open the tubular reactor 4 and heat the tubular reactor 4 to raise the temperature of the system to 90° C.

3) Open the raw material storage tank 1 to introduce

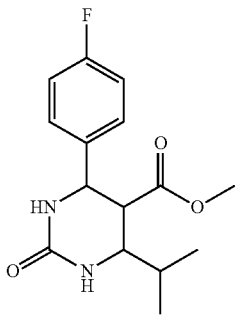 [SMILES: COC(=O)C1C(c2ccc(F)cc2)NC(=O)NC1C(C)C]

into the tubular reactor 4 at a feed rate of 100 kg/h.

4) Open the nitric acid solution storage tank again to continue to introduce the nitric acid solution into the tubular reactor 4 at a feed rate of 33 kg/h.

5) Open all venturi nozzles 3 to feed oxygen into the tubular reactor 4 at a total feed rate of 9.1 m³/h.

6) Open the intermediate tank 8 for the reaction mixture to discharge the excess effluent in the tubular reactor 4 at a discharge rate of 30 kg/h.

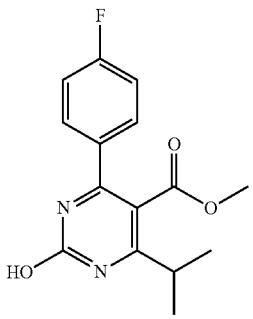 [SMILES: COC(=O)c1c(-c2ccc(F)cc2)nc(O)nc1C(C)C]

7) Open the screw conveyor 6 to transport the synthesized in the tubular filter 5 into the product storage tank 7; wash the product in the storage tank with water and dry it; and finally analyze it by a high performance liquid chromatography; A purity of

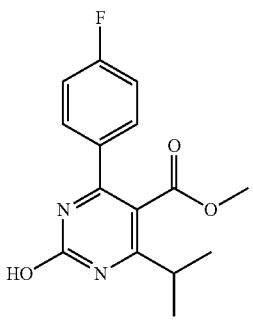 [SMILES: COC(=O)c1c(-c2ccc(F)cc2)nc(O)nc1C(C)C]

is 99.5%; a production rate is 95.3 kg/h; and a molar yield is 96.5%.

8) Check and keep the concentration of nitric acid in the reaction mixture in the intermediate tank 8 every hour at no less than 63.7%. When the concentration of nitric acid is lower than 63.7%, the feed rate of nitric acid solution needs to be increased appropriately.

The above-mentioned embodiments are only for illustrative purposes, and are not intended to limit the scope of the present disclosure. Any improvements, changes, modifications without departing from the spirit of the present invention shall fall within the scope of the present invention.

What is claimed is:

1. A metal-free catalytic oxidation system, comprising:
a feed device;
a tubular reactor;
a plurality of venturi nozzles mounted on the tubular reactor at intervals;
a tubular filter;
a discharge device for a solid phase product connected to a solid phase output end of the tubular filter; and
an intermediate tank for reaction mixture connected to a liquid phase output end of the tubular filter;
wherein a low-pressure zone is formed at an output end of each of the plurality of venturi nozzles, and an oxygen inlet corresponds to the low-pressure zone; the tubular filter comprises an inner tube and an outer tube connected to each other, wherein the inner tube is provided with small holes for solid-liquid separation; the discharge device for the solid phase product is located at an end of the inner tube; and the intermediate tank for reaction mixture is connected to the outer tube of the tubular filter through a pipeline.

2. The system of claim 1, wherein the feed device comprises a basic material feed device and a nitric acid feed device.

3. The system of claim 1, wherein a heat exchange system in the form of a sleeve is provided outside the tubular reactor, and a heat exchange medium flows in a gap between the heat exchange system and the tubular reactor.

4. The system of claim 1, wherein the plurality of venturi nozzles are spaced apart on the tubular reactor.

5. The system of claim 1, wherein the discharge device for the solid phase product is a screw conveyor.

6. The system of claim 1, wherein the intermediate tank for reaction mixture is provided with two bleeder tubes, where one is connected to an effluent treatment system, and the other is connected to the tubular reactor.

7. The system of claim 1, wherein the tubular reactor is provided with a circulating feed pump.

8. An oxygenation method using the metal-free catalytic oxidation system of claim 1.

9. A method for producing benzoic acid derivatives by oxygenation using the metal-free catalytic oxidation system of claim 6, comprising:
1) opening a nitric acid storage tank to add a certain amount of a nitric acid and then closing the nitric acid storage tank; and turning on the circulating feed pump to start circulation of materials in the system;
2) turning on a heat exchange system of the tubular reactor to heat the tubular reactor;
3) opening a raw material storage tank to introduce a raw material into the tubular reactor;
4) opening the nitric acid storage tank again to introduce the nitric acid into the tubular reactor;
5) opening the plurality of venturi nozzles to feed oxygen, the raw material and the nitric acid into the tubular reactor for reaction;
6) opening the intermediate tank for the reaction mixture to discharge excess effluent in the tubular reactor; and 7) turning on the screw conveyor to transport finished product in the tubular filter into a product storage tank.
10. A method for producing benzoic acid derivatives by oxygenation using the metal-free catalytic oxidation system of claim 1, wherein the raw material is any one of tert-butyltoluene, nitrotoluene, p-chlorotoluene,
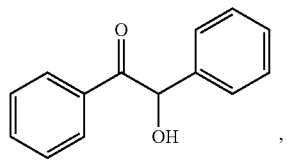 [SMILES: O=C(c1ccccc1)C(O)c1ccccc1]
,
2,4-dimethyl nitrobenzene,
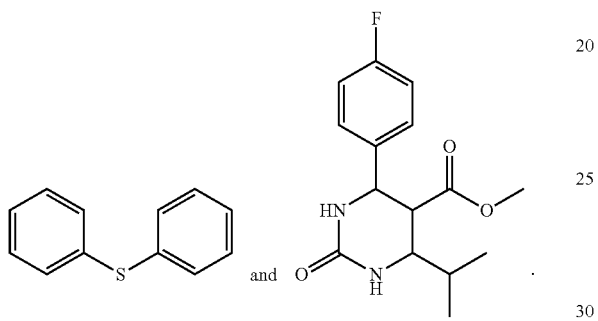
.
* * * * *